US011666753B2

(12) United States Patent
Shuros et al.

(10) Patent No.: US 11,666,753 B2
(45) Date of Patent: Jun. 6, 2023

(54) MULTIPOLAR LEAD FOR HIS BUNDLE PACING

(71) Applicant: Cardiac Pacemakers, Inc., St. Paul, MN (US)

(72) Inventors: Allan C. Shuros, St. Paul, MN (US); Arthur J. Foster, Blaine, MN (US); Keith L. Herrmann, Minneapolis, MN (US); Deepa Mahajan, North Oaks, MN (US); Stephen J. Hahn, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 17/592,884

(22) Filed: Feb. 4, 2022

(65) Prior Publication Data

US 2022/0211998 A1  Jul. 7, 2022

Related U.S. Application Data

(63) Continuation of application No. 16/389,334, filed on Apr. 19, 2019, now Pat. No. 11,318,303.

(Continued)

(51) Int. Cl.
*A61N 1/05* (2006.01)
*A61N 1/36* (2006.01)

(52) U.S. Cl.
CPC .................................. *A61N 1/059* (2013.01)

(58) Field of Classification Search
CPC .. A61N 1/0573; A61N 1/059; A61N 1/36114; A61N 1/3684; A61N 1/3606;

(Continued)

(56) References Cited

U.S. PATENT DOCUMENTS

| 4,214,804 A | 7/1980 | Little |
| 4,886,074 A | 12/1989 | Bisping |

(Continued)

FOREIGN PATENT DOCUMENTS

WO 2004/069329 A1 8/2004

OTHER PUBLICATIONS

International Search Report and Written Opinion issued in PCT/US2019/028302, dated Jul. 19, 2019, 12 pages.

(Continued)

*Primary Examiner* — Carl H Layno
*Assistant Examiner* — Anh-Khoa N Dinh
(74) *Attorney, Agent, or Firm* — Nelson Mullins Riley & Scarborough LLP (57) ABSTRACT

A device for the active fixation of an implantable medical lead includes a housing, a tine assembly, an electrode, and a rotatable shaft. The housing includes a proximal end for connecting to the lead and a distal end opposite the proximal end. The housing defines a housing lumen extending between the proximal end and a recess adjacent to the distal end. The tine assembly is disposed within the housing lumen and includes at least one tine configured to self-bias from a linear configuration within the housing to a curved configuration outside of the housing. The electrode assembly is disposed at the distal end of the housing and includes a plurality of electrodes. The rotatable shaft extends through the housing lumen and is configured to engage the tine assembly such that rotation of the shaft transitions the at least one tine between the linear configuration and the curved configuration.

20 Claims, 6 Drawing Sheets

Related U.S. Application Data (60) Provisional application No. 62/661,516, filed on Apr. 23, 2018.

(58) Field of Classification Search
CPC ............ A61N 1/36062; A61N 1/36064; A61N 1/36067; A61N 1/36071; A61N 1/36078; A61N 1/36082; A61N 1/36103
See application file for complete search history.

(56) References Cited

U.S. PATENT DOCUMENTS

| | | | |
|---|---|---|---|
| 5,095,916 A * | 3/1992 | Smits | A61N 1/0587 607/116 |
| 5,353,800 A | 10/1994 | Pohndorf et al. | |
| 5,492,119 A | 2/1996 | Abrams | |
| 6,704,605 B2 | 3/2004 | Soltis et al. | |
| 7,177,704 B2 | 2/2007 | Laske et al. | |
| 7,212,870 B1 | 5/2007 | Helland | |
| 7,212,871 B1 | 5/2007 | Morgan | |
| 7,319,905 B1 | 1/2008 | Morgan et al. | |
| 7,369,901 B1 | 5/2008 | Morgan et al. | |
| 7,418,298 B2 | 8/2008 | Shiroff et al. | |
| 7,433,739 B1 | 10/2008 | Salys et al. | |
| 7,496,410 B2 | 2/2009 | Heil, Jr. | |
| 7,546,166 B2 | 6/2009 | Michels et al. | |
| 7,657,326 B2 | 2/2010 | Bodner et al. | |
| 7,711,437 B1 | 5/2010 | Bornzin et al. | |
| 7,751,905 B2 | 7/2010 | Feldmann et al. | |
| 7,860,581 B2 | 12/2010 | Eckerdal et al. | |
| 7,920,927 B2 | 4/2011 | Zarembo et al. | |
| 7,920,928 B1 | 4/2011 | Yang et al. | |
| 8,000,805 B2 | 8/2011 | Swoyer et al. | |
| 8,036,756 B2 | 10/2011 | Swoyer et al. | |
| 8,036,757 B2 | 10/2011 | Worley | |
| 8,090,451 B2 | 1/2012 | Tyson, Jr. | |
| 8,346,374 B2 | 1/2013 | Foster et al. | |
| 8,406,899 B2 | 3/2013 | Reddy et al. | |
| 9,008,768 B2 | 4/2015 | Zhu et al. | |
| 9,302,098 B2 | 4/2016 | Zhang et al. | |
| 9,545,513 B2 | 1/2017 | Hastings et al. | |
| 9,579,501 B2 | 2/2017 | Shuros et al. | |
| 11,318,303 B2 | 5/2022 | Shuros et al. | |
| 2003/0204233 A1 | 10/2003 | Laske et al. | |
| 2004/0054388 A1 * | 3/2004 | Osypka | A61N 1/056 607/116 |
| 2004/0215307 A1 | 10/2004 | Michels et al. | |
| 2005/0113900 A1 | 5/2005 | Shiroff et al. | |
| 2006/0106315 A1 | 5/2006 | Edens | |
| 2006/0129218 A1 | 6/2006 | Swoyer et al. | |
| 2006/0155353 A1 | 7/2006 | Heil | |
| 2007/0050003 A1 * | 3/2007 | Zarembo | A61N 1/057 607/116 |
| 2007/0050004 A1 | 3/2007 | Swoyer et al. | |
| 2007/0106202 A1 | 5/2007 | Salo et al. | |
| 2007/0129782 A1 | 6/2007 | Feldmann et al. | |
| 2007/0239241 A1 | 10/2007 | Tyson | |
| 2008/0065185 A1 | 3/2008 | Worley | |
| 2008/0109042 A1 | 5/2008 | Bodner et al. | |
| 2008/0249596 A1 | 10/2008 | Shiroff et al. | |
| 2008/0262588 A1 | 10/2008 | Zarembo et al. | |
| 2008/0288040 A1 | 11/2008 | Eckerdal et al. | |
| 2009/0259272 A1 | 10/2009 | Reddy et al. | |
| 2010/0305670 A1 | 12/2010 | Hall et al. | |
| 2010/0324644 A1 | 12/2010 | Levi et al. | |
| 2011/0009939 A1 | 1/2011 | Foster et al. | |
| 2011/0160817 A1 | 6/2011 | Foster et al. | |
| 2011/0199173 A1 | 8/2011 | Leijssen et al. | |
| 2011/0251662 A1 | 10/2011 | Griswold et al. | |
| 2012/0004714 A1 | 1/2012 | Kleve et al. | |
| 2012/0179221 A1 | 7/2012 | Reddy et al. | |
| 2013/0261689 A1 | 10/2013 | Zhu et al. | |
| 2013/0296852 A1 | 11/2013 | Madjarov et al. | |
| 2014/0067036 A1 | 3/2014 | Shuros et al. | |
| 2014/0107755 A1 | 4/2014 | Ollivier | |
| 2014/0207149 A1 | 7/2014 | Hastings et al. | |
| 2014/0243946 A1 | 8/2014 | Zhang et al. | |
| 2015/0080995 A1 | 3/2015 | Seeley et al. | |
| 2015/0105729 A1 | 4/2015 | Valeti et al. | |
| 2015/0313669 A1 | 11/2015 | Darmos et al. | |
| 2016/0331957 A1 | 11/2016 | Gindele et al. | |
| 2017/0043158 A1 | 2/2017 | Kelly et al. | |
| 2017/0106185 A1 | 4/2017 | Orts et al. | |
| 2019/0022379 A1 | 1/2019 | Foster et al. | |
| 2019/0321625 A1 | 10/2019 | Shuros et al. | |
| 2020/0114146 A1 | 4/2020 | Foster et al. | |

OTHER PUBLICATIONS

International Search Report and Written Opinion issued in PCT/US2019/056095, dated Jan. 28, 2020, 14 pages.

Search Report and Written Opinion issued in NL Application 2019577, dated Mar. 1, 2018, 7 pages.

* cited by examiner

MULTIPOLAR LEAD FOR HIS BUNDLE PACING

CROSS-REFERENCE TO RELATED APPLICATION

This application is a continuation application of U.S. patent application Ser. No. 16/389,334, now U.S. Patent No. 11,318,303 B2, filed Apr. 19, 2019, which claims priority to Provisional Application 62/661,516, filed Apr. 23, 2018, which is herein incorporated by reference in its entirety.

TECHNICAL FIELD

The present disclosure relates to medical devices and methods for the active fixation of an implantable medical lead. More specifically, the disclosure relates to devices and methods for active fixation of implantable medical leads for mapping and stimulating the bundle of His in patient's heart.

BACKGROUND

Cardiac rhythm management systems are useful for electrically stimulating a patient's heart to treat various cardiac arrhythmias. A method of electrically stimulating the heart can include stimulating the His bundle at a location proximate to the tricuspid valve at the interatrial septum in the right atrium of the heart or at a location proximate to the tricuspid valve at the interventricular septum in the right ventricle of the heart. Directly stimulating the bundle of His can simultaneously pace both the right and left ventricles of the heart, potentially avoiding pacing induced dyssynchrony which may occur with right ventricular apex pacing. There is a continuing need for improved His bundle lead designs and assemblies.

SUMMARY

Example 1 is a device for the active fixation of an implantable medical lead. The device includes a housing, a tine assembly, an electrode, and a rotatable shaft. The housing includes a proximal end for connecting to the lead and a distal end opposite the proximal end. The housing defines a housing lumen having a longitudinal axis. The housing lumen extends between the proximal end and a recess adjacent to the distal end. The tine assembly is disposed within the housing lumen. The tine assembly includes at least one tine configured to self-bias from a linear configuration within the housing to a curved configuration outside of the housing. The electrode assembly is disposed at the distal end of the housing. The electrode assembly includes a plurality of electrodes. The rotatable shaft extends through the housing lumen. The shaft is configured to engage the tine assembly such that rotation of the shaft transitions the at least one tine between the linear configuration and the curved configuration.

Example 2 is the device of Example 1, wherein the housing further includes internal screw threads extending along the housing lumen, and the tine assembly further includes a driver member and a carrier member. The driver member is disposed within the housing lumen. The driver member defines a driver lumen coaxial with the housing lumen. The driver member includes a threaded portion having external screw threads engaged with the internal screw threads of the housing, a flange; and a hub connecting the flange to the threaded portion. The carrier member is rotatably disposed around the hub of the driver member. The at least one tine is connected to and projects from the carrier member. The rotatable shaft extends through the driver lumen. The shaft is configured to engage the driver member such that rotation of the shaft rotates the driver member to transition the at least one tine between the linear configuration and the curved configuration.

Example 3 is the device of Example 2, wherein the flange and the threaded portion of the driver member constrain axial movement of the carrier member.

Example 4 is the device of either of Examples 2 or 3, wherein the housing further defines at least one slot at least partially radially outward from the internal screw threads, the at least one slot extending from the proximal end to the distal end and parallel to the longitudinal axis.

Example 5 is the device of Example 4, wherein the carrier member includes at least one lobe configured to engage the at least one slot to prevent axial rotation of the carrier member relative to the housing while permitting the carrier member to move through the housing lumen while the shaft rotates the driver member, the at least one tine connected to and projecting from the at least one lobe.

Example 6 is the device of any of Examples 2-5, wherein the driver lumen is sized so that the driver member can slide along the shaft while the shaft rotates the driver member.

Example 7 is the device of any of Examples 1-6, wherein rotation of the shaft in a first direction moves the at least one tine out of the housing lumen, transitioning the at least one tine from the linear configuration to the curved configuration to fix the lead to tissue, and rotation of the shaft in a second direction opposite the first direction retracts the at least one tine into the housing lumen, transitioning the at least one tine from the curved configuration to the linear configuration.

Example 8 is the device of any of Examples 1-7, wherein the at least one tine includes a plurality of tines.

Example 9 is the device of any of Examples 1-8, wherein the plurality of electrodes includes a conical tip electrode and an anode electrode proximal of the conical tip electrode.

Example 10 is the device of any of Examples 1-9, wherein the electrode assembly is collinear with the longitudinal axis of the housing lumen.

Example 11 is the device of any of Examples 1-10, wherein the shaft is electrically and mechanically isolated from the electrode assembly.

Example 12 is an implantable medical lead including flexible, tubular lead body, a connector assembly, a plurality of electrical conductors, and a device for the active fixation of the implantable medical lead according to any of Examples 1-11. The lead body includes a proximal end and a distal end. The connector assembly is disposed at the proximal end. The plurality of electrical conductors extends from the connector assembly to the distal end. The device for the active fixation of the implantable medical lead is disposed at the distal end of the lead body. The plurality of electrical conductors is electrically connected to the electrode assembly.

Example 13 is a method of making a device for the active fixation of an implantable medical lead. The method includes attaching at least one tine to a carrier member, the tine self-biasing to a curved configuration; inserting a hub extending from a threaded portion of a driver member through the carrier member such that the carrier member is rotatable about the hub; forming a flange at an end of the hub opposite the threaded portion of the driver member, the flange and the threaded portion of the driver member restraining the axial movement of the carrier member; inserting the at least one tine into a proximal end of a longitudinal slot of a housing lumen of a housing to place the at least one tine in a linear configuration contained by the housing; threading the threaded portion of the drive member into a threaded portion at a proximal end of the housing; inserting a shaft through the a driver lumen of the driver member at the proximal end of the housing and through the housing lumen to a recess adjacent to a distal end of the housing; and connecting an electrode assembly to the distal end of the housing, the electrode assembly including a plurality of electrodes.

Example 14 is the method of Example 13, further including electrically connecting each of the plurality of electrodes to separate electrical conductors.

Example 15 is the method of either of Examples 13 or 14, wherein forming the flange at the end of the hub includes heating the end of the hub until it softens and flanging the heated hub outward to form the flange.

Example 16 is a device for the active fixation of an implantable medical lead into tissue. The device includes a housing, a tine assembly, an electrode assembly, and a rotatable shaft. The housing includes a proximal end for connecting to the lead and a distal end opposite the proximal end. The housing defines a housing lumen having a longitudinal axis. The housing lumen extends between the proximal end and a recess adjacent to the distal end. The tine assembly is disposed within the housing lumen. The tine assembly includes at least one tine configured to self-bias from a linear configuration within the housing to a curved configuration outside of the housing. The electrode assembly is disposed at the distal end of the housing. The electrode assembly includes a conical tip electrode and an anode electrode proximal of the conical tip electrode. The rotatable shaft extends through the housing lumen. The shaft is configured to engage the tine assembly such that rotation of the shaft transitions the at least one tine between the linear configuration and the curved configuration.

Example 17 is the device of Example 16, wherein rotation of the shaft in a first direction moves the at least one tine out of the housing lumen, transitioning the at least one tine from the linear configuration to the curved configuration to fix the lead to tissue, and rotation of the shaft in a second direction opposite the first direction retracts the at least one tine into the housing lumen, transitioning the at least one tine from the curved configuration to the linear configuration to release the lead from tissue.

Example 18 is the device of either of Examples 16 or 17, wherein a proximal end of the shaft includes a structure for engaging a stylet.

Example 19 is the device of any of Examples 16-18, wherein the at least one tine includes a plurality of tines.

Example 20 is the device of any of Examples 16-19, wherein the anode electrode is electrically isolated from the conical tip electrode.

Example 21 is the device of any of Examples 16-20, wherein the electrode assembly is collinear with the longitudinal axis of the housing lumen.

Example 22 is the device of any of Examples 16-21, wherein the housing further includes internal screw threads extending along the housing lumen, and the tine assembly further includes a driver member and a carrier member. The driver member is disposed within the housing lumen. The driver member defines a driver lumen coaxial with the housing lumen. The driver member includes a threaded portion having external screw threads engaged with the internal screw threads of the housing, a flange, and a hub connecting the flange to the threaded portion. The carrier member is rotatably disposed around the hub of the driver member. The at least one tine is connected to, and projects from, the carrier member. The rotatable shaft extends through the driver lumen. The shaft is configured to engage the driver member such that rotation of the shaft rotates the driver member to transition the at least one tine between the linear configuration and the curved configuration.

Example 23 the device of Example 22, wherein the flange and the threaded portion of the driver member constrain axial movement of the carrier member.

Example 24 the device of either of Examples 22 or 23, wherein the housing further defines at least one slot at least partially radially outward from the internal screw threads, the at least one slot extending from the proximal end to the distal end and parallel to the longitudinal axis.

Example 25 is the device of Example 24, wherein the carrier member includes at least one lobe configured to engage the at least one slot to prevent axial rotation of the carrier member relative to the housing while permitting the carrier member to move through the housing lumen while the shaft rotates the driver member, the at least one tine connected to and projecting from the at least one lobe.

Example 26 is the device of any of Examples 22-25, wherein the driver lumen is sized so that the driver member can slide along the shaft while the shaft rotates the driver member.

Example 27 is an implantable medical lead including a flexible, tubular lead body including a proximal end and a distal end, a connector assembly connector disposed at the proximal end, a plurality of electrical conductors extending through the tubular body from the connector assembly to the distal end, and a device for the active fixation of the implantable medical lead, the device disposed at the distal end of the lead. The device includes a housing, a tine assembly, an electrode assembly, and a rotatable shaft. The housing including a proximal end for connecting to the lead and a distal end opposite the proximal end. The housing defines a housing lumen having a longitudinal axis. The housing lumen extends between the proximal end and a recess adjacent to the distal end. The tine assembly is disposed within the housing lumen. The tine assembly includes at least one tine configured to self-bias from a linear configuration within the housing to a curved configuration outside of the housing. The electrode assembly is disposed at the distal end of the housing. The electrode assembly includes a conical tip electrode electrically connected to at least one of the plurality of electrical conductors, an anode electrode proximal of the conical tip electrode, and a rotatable shaft extending through the housing lumen from the proximal end to the recess adjacent to the distal end. The anode electrode is electrically connected to at least one of the plurality of electrical conductors different from the at least one of the plurality of electrical conductors electrically connected to the conical tip electrode. The rotatable shaft is configured to engage the tine assembly such that rotation of the shaft transitions the at least one tine between the linear configuration and the curved configuration.

Example 28 is the lead of Example 27, wherein the at least one tine includes a plurality of tines.

Example 29 the lead of either of Examples 27 or 28, wherein the anode electrode is electrically isolated from the conical tip electrode.

Example 30 is the lead of any of examples Example 27-29, wherein the housing further includes internal screw threads extending along the housing lumen, and the tine assembly further includes a drive member and a carrier member. The driver member is disposed within the housing lumen. The driver member defines a driver lumen coaxial with the housing lumen. The driver member includes a threaded portion having external screw threads engaged with the internal screw threads of the housing, a flange, and a hub connecting the flange to the threaded portion. The carrier member is rotatably disposed around the hub of the driver member. The at least one tine is connected to, and projects from, the carrier member. The rotatable shaft extends through the driver lumen. The shaft is configured to engage the driver member such that rotation of the shaft rotates the driver member to transition the at least one tine between the linear configuration and the curved configuration. The flange and the threaded portion of the driver member constrain axial movement of the carrier member.

Example 31 is the lead of Example 30, wherein the housing further defines at least one slot at least partially radially outward from the internal screw threads, the at least one slot extending from the proximal end to the distal end and parallel to the longitudinal axis, and the carrier member includes at least one lobe configured to engage the at least one slot to prevent axial rotation of the carrier member relative to the housing while permitting the carrier member to move through the housing lumen while the shaft rotates the driver member, the at least one tine connected to and projecting from the at least one lobe.

Example 32 is a method of making a device for the active fixation of an implantable medical lead. The method includes attaching at least one tine to a carrier member, the tine self-biasing to a curved configuration; inserting a hub extending from a threaded portion of a driver member through the carrier member such that the carrier member is rotatable about the hub; forming a flange at an end of the hub opposite the threaded portion of the driver member, the flange and the threaded portion of the driver member restraining the axial movement of the carrier member; inserting the at least one tine into a proximal end of a longitudinal slot of a housing lumen of a housing to place the at least one tine in a linear configuration contained by the housing; threading the threaded portion of the drive member into a threaded portion at a proximal end of the housing; inserting a shaft through the a driver lumen of the driver member at the proximal end of the housing and through the housing lumen to a recess adjacent to a distal end of the housing; and connecting an electrode assembly to the distal end of the housing, the electrode assembly including a plurality of electrodes.

Example 33 is the method of Example 32, further including electrically connecting each of the plurality of electrodes to separate electrical conductors.

Example 34 is the method of either of Examples 32 or 33, wherein forming the flange at the end of the hub includes heating the end of the hub until it softens and flanging the heated hub outward to form the flange.

Example 35 is the method of either of Examples 32 or 33, wherein forming the flange at the end of the hub includes connecting the flange to the end of the hub While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
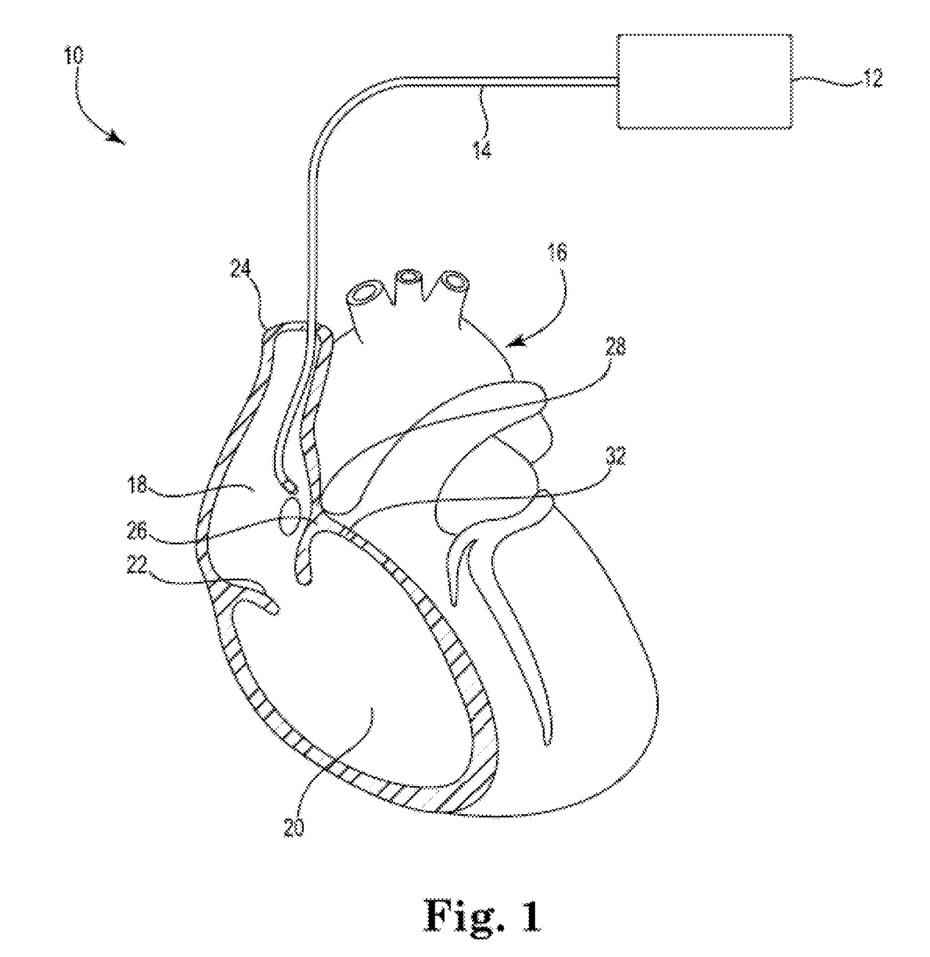
FIG. 1 is a schematic view of system for mapping and stimulating the bundle of His in a patient's heart, including a lead according to embodiments of this disclosure.

FIG. 1 is a schematic view of system 10 for mapping and stimulating the bundle of His, according to embodiments of this disclosure. As shown in FIG. 1, the system 10 includes an implantable pulse generator 12 coupled to a lead 14 deployed in a patient's heart 16. The pulse generator 12 generates an electrical pacing stimulus to be delivered to the heart 16. The lead 14 operates to convey electrical signals and stimuli between the heart 16 and the pulse generator 12. As further shown in FIG. 1, the heart 16 includes a right atrium 18 and a right ventricle 20 separated by a tricuspid valve 22. In the embodiment shown in FIG. 1, the lead 14 enters the vascular system through a vascular entry site (not shown) and a superior vena cava 24 to be implanted in the right atrium 18. The bundle of His 26 can be stimulated at an atrial location proximate to the tricuspid valve 22 at an interatrial septum 28 in the right atrium 18, as shown in FIG. 1. This location is proximate to the apex of the triangle of Koch. Alternatively, the bundle of His 24 can be stimulated at a ventricular location proximate to the tricuspid valve 22 at an interventricular septum 32 in the right ventricle 20 by passing the lead 14 through the tricuspid valve 22 and into the right ventricle 20.

The system 10 allows direct therapeutic stimulation of the bundle of His 26 by fixating the lead 14 at one of the locations describe above. Mapping at one of the locations described above is necessary to be able to positioning of the lead 14 close enough to the bundle of His 26 for efficient and effective pacing. Some prior art leads rely on non-contact sensing or surface contact sensing with electrodes to map the location of the bundle of His 26. However, in some instances, this may not be accurate enough to identify the proper location to implant the lead 14. Such precise mapping can require repeated penetration of the myocardium to achieve the sensitivity necessary to accurately locate the bundle of His 26. In some other prior art leads, a helical electrode can be employed to repeatedly penetrate the myocardium to locate the bundle of His 26. However, repeatedly implanting and removing the helical electrode, which requires multiple rotations of the helical electrode, can be time consuming and may damage the myocardium. In addition, once a suitable location is found, the recoil from the force required to implant the helical electrode to fixate the prior art lead can result in the helical electrode moving from the identified location and being implanted in a less suitable location. Embodiments of the present disclosure permit mapping that is faster and less harmful to the myocardium, while employing a fixation device that accurately secures a lead electrode in the myocardium and an electrode assembly that can provide a higher current density at the bundle of His 26.

Figure 2:
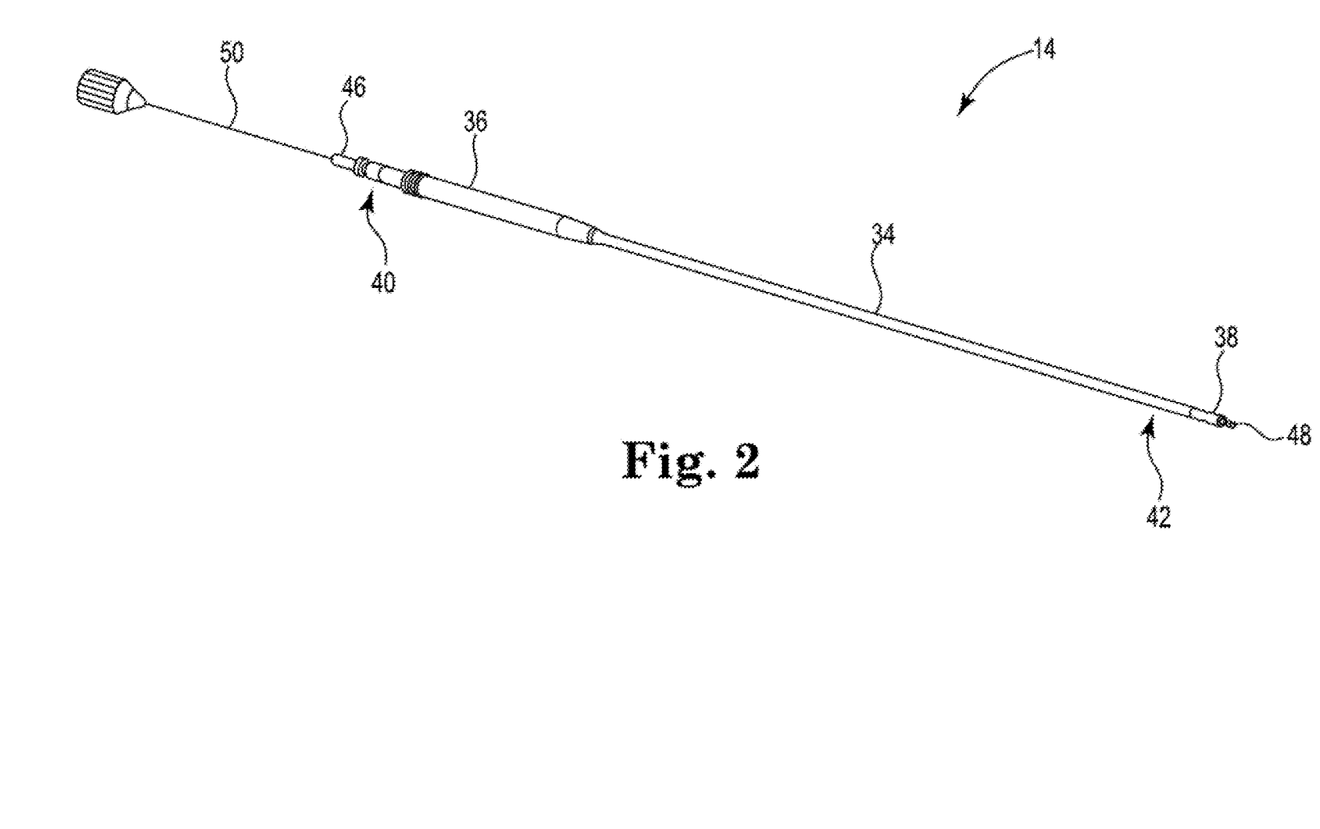
FIG. 2 is a perspective view of the lead of FIG. 1, according to embodiments of this disclosure.

FIG. 2 is a perspective view of the lead 14 of FIG. 1, according to embodiments of this disclosure. As shown in FIG. 2, the lead 14 includes a lead body 34, a connector assembly 36, and a fixation device 38. The lead body 34 is a flexible tubular body including a proximal end 40 and a distal end 42, and containing a first electrical conductor 44 and a second electrical conductor 45 (FIG. 3) each extending from the proximal end 40 to the distal end 42. The connector assembly 36 is disposed at the proximal end 40 and includes a terminal pin 46 electrically connected to the first electrical conductor 44 and the second electrical conductor 45. The connector assembly 36 is configured to electrically couple the lead 14 to the pulse generator 12 (FIG. 1). The fixation device 38 is a device for the active fixation of the lead 14. The fixation device 38 is disposed at the distal end 42 of the lead 14 and includes an electrode assembly 48. In the embodiment of FIG. 2, the first electrical conductor 44 and the second electrical conductor 45 are electrically connected to the electrode assembly 48 so that it can function as an active bipolar electrode to stimulate the bundle of His 26 (FIG. 1).

In some embodiments, the first electrical conductor 44 and the second coil conductor 45 are filars of a bifilar or multi-filar coil conductor. In some embodiments, a stylet 50 can be extended through connector assembly 36 and the lead body 34 to the fixation device 38 and engage the fixation device 38 such that rotation of the stylet 50 causes the fixation device 38 to fixate the lead 14, as described below.

Figure 3:
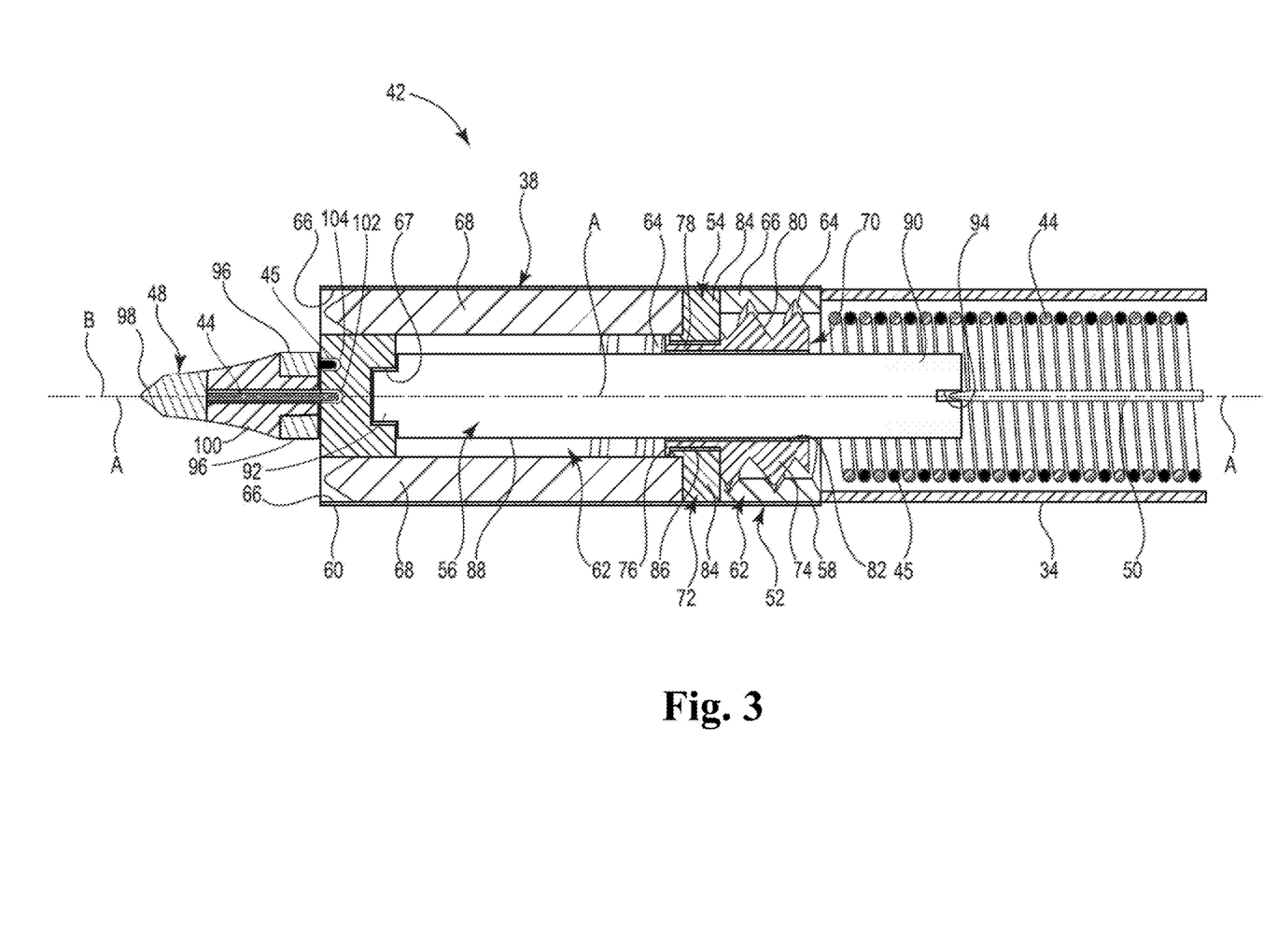
FIG. 3 is schematic cross-sectional view of a distal end of the lead of FIG. 2 showing a device for the active fixation of the lead in an undeployed state, according to embodiments of this disclosure.

FIG. 3 is schematic cross-sectional view of the distal end 42 of the lead 14 of FIG. 2 including the fixation device 38, according to embodiments of this disclosure. In FIG. 3, the fixation device 38 is shown in an undeployed stated. As shown in FIG. 3, in addition to the electrode assembly 48, the fixation device 38 can further include a housing 52, a tine assembly 54, and a rotatable shaft 56. The housing 52 can include a proximal end 58 and a distal end 60 opposite the proximal end 58. The housing 52 can define a housing lumen 62, internal screw threads 64, and at least one slot 66 (two shown in FIG. 3, four shown in FIGS. 6 and 7). The housing lumen 62 can include a recess 67 at the distal end 60 and have a longitudinal axis A extending between the proximal end 58 and the distal end 60 of the housing 52. The internal screw threads 64 can extend along a portion of the housing lumen 62 from the proximal end 58 of the housing 52. The at least one slot 66 is formed at least partially radially outward from the internal screw threads 64 and extends longitudinally from the proximal end 58 to the distal end 60 of the housing 52 and is parallel to the longitudinal axis A. The housing 52 can be made of a biocompatible polymer that is rigid at body temperature, such as polyetheretherketone (PEEK) or polyethersulfone (PES). The housing 52 can be formed by, for example, molding, machining, or 3D additive manufacturing.

Figure 4:
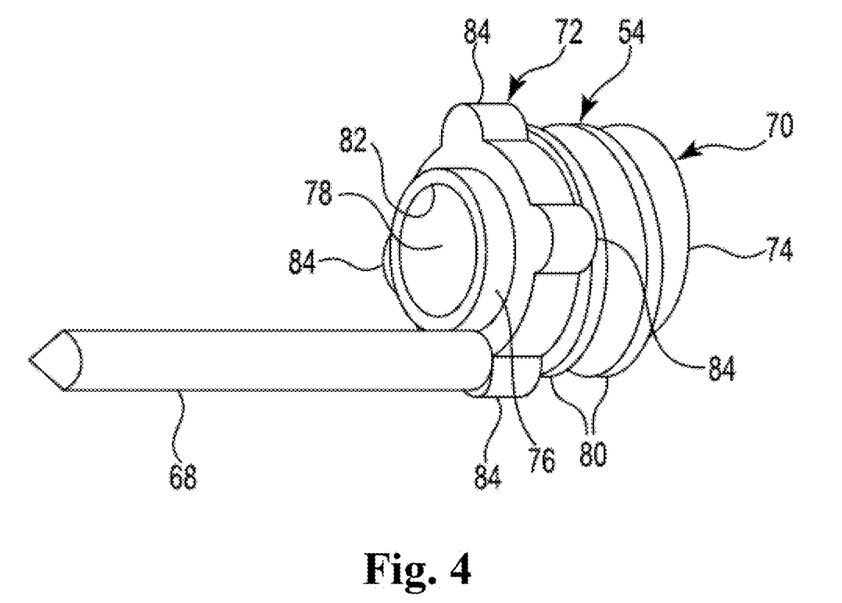
FIG. 4 is a perspective view of some of a tine assembly of FIG. 3 for the active fixation of the lead, according to embodiments of this disclosure.

FIG. 4 is a perspective view the tine assembly 54 of FIG. 3, according to embodiments of this disclosure. Considering FIGS. 3 and 4 together, the tine assembly 54 can include at least one tine 68, a driver member 70, and a carrier member 72. The embodiment of FIGS. 3 and 4 includes four tines 68 (FIG. 6), two shown in FIG. 3, one shown in FIG. 4 with the remaining three omitted for clarity. The at least one tine 68 is formed of a material having a shape memory, for example nitinol or a gold/stainless steel alloy, such that the at least one tine 68 can biased to be curved configuration when unrestrained and outside of the housing 52 (FIG. 6) and can be in a linear configuration when restrained by the housing 52, as shown in FIGS. 3 and 4. The at least one tine 68 can be pointed for ease in entering tissue for fixation.

The driver member 70 can include a threaded portion 74, a flange 76, and a hub 78. The threaded portion 74 includes external screw threads 80 for threaded engagement with the internal screw threads 64 of the housing 52. The hub 78 connects the flange 76 to the threaded portion 74. The flange 76 extends radially outward from the hub 78. The driver member 70 can also define a driver lumen 82 extending through the threaded portion 74, the hub 78 and the flange 76. The driver lumen 82 can be coaxial with the housing lumen 62 as shown in FIG. 3.

In some embodiments, such as the embodiment shown in FIG. 3, the driver member 70 can be a one-piece, monolithic structure. In such embodiments, the flange 76 can be formed shaping, or flanging, an end of the hub 78 opposite the threaded portion 74 radially outward to form the flange 76. In some embodiments, the end of the hub 78 may need to be heated until it softens, before flanging the heated end of the hub 78 outward to form the flange 76. In other embodiments, the driver member 70 can be a two-piece structure in which the flange 76 and the hub 78 may be a single piece that connects to the threaded portion 74 by, for example, a snap joint or an adhesive joint. Alternatively, the hub 78 and the threaded portion 74 may be a single piece that connects to the flange 76 by, for example, an adhesive joint or a weld.

The driver member 70 can be made of a biocompatible metal, such as stainless steel, Elgiloy, MP35N, or titanium, or a biocompatible polymer that is rigid at body temperature, such as polyetheretherketone (PEEK) or polyethersulfone (PES), or a combination of any of the foregoing materials. The driver member 70 can be formed by, for example, molding, machining, or 3D additive manufacturing. In some embodiments, should the at least one tine 68 and the driver member 70 be formed of conductive materials, the flange 76 can be adequately spaced from the at least one tine 68 so that the electrode assembly 48 and the shaft 56 are electrically insulated from the at least one tine 68. In some embodiments in which the driver member 70 is a two-piece structure, the threaded portion 74 can be formed of a metal while the flange 76 is formed of a non-conductive polymer to maintain electrical isolation between the shaft 56 and the at least one tine 68.

Figure 5:
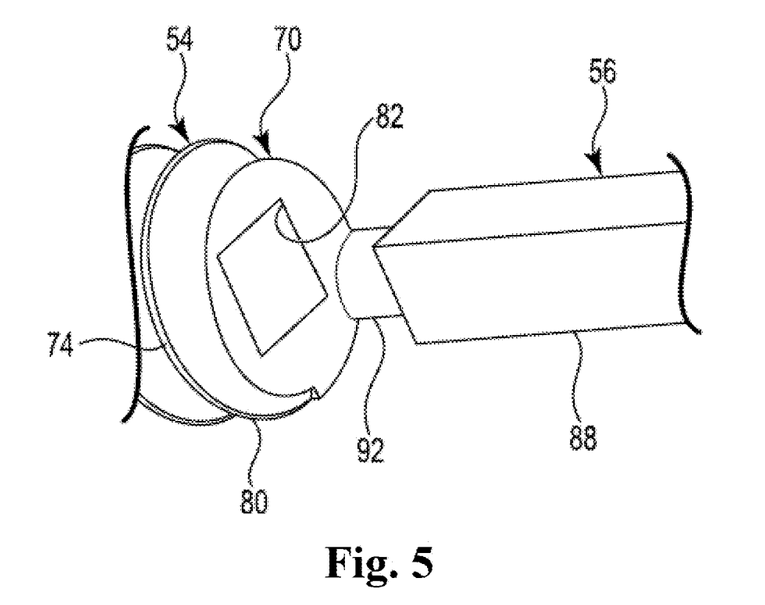
FIG. 5 is an exploded perspective view of an end of the tine assembly and a rotatable shaft of FIG. 3, according to embodiments of this disclosure.

The carrier member 72 can include at least one lobe 84 (two shown in FIG. 3, four in the embodiment of FIG. 3, as shown in FIG. 5) at a circumference of the carrier member 72. The at least one tine 68 can be attached to, and project from the at least one lobe 84. In the embodiment of FIGS. 3 and 5, each of the four tines 68 is attached to one of the four lobes 84. The tines 68 can be attached by, for example, molding the lobes 84 around the tines 68, as shown in FIG. 3. Alternatively, the tines 68 can be attached to the lobes 84 by a mechanical fastener, adhesive, or other suitable means. The carrier member 72 can define a carrier lumen 86 through which the hub 78 passes. An inner diameter of the carrier lumen 86 is sufficiently larger than an outer diameter of the hub 78 such that the carrier member 72 is rotatably disposed around the hub 78. As shown in FIG. 3, so configured, the flange 76 and the threaded portion 74 constrain the movement of the carrier member 72 in the axial direction, but not so tightly as to prevent or interfere with the ability of the carrier member 72 to rotate relative to the hub 78.

The carrier member 72 can be made of a biocompatible polymer that is rigid at body temperature and will thread well through the housing 52 without sticking, such as polyoxymethylene (POM) or polyetheretherketone (PEEK). The carrier member 72 can be formed by, for example, molding, machining, or 3D additive manufacturing.

FIG. 5 is an exploded perspective view of an end of the tine assembly 54 and the shaft 56, according to embodiments of this disclosure. As shown in the embodiment of FIG. 5, the main shaft portion 88 can have a square cross-sectional shape, while the distal shaft portion 92 can have a circular cross-sectional shape. The driver lumen 82 through the threaded portion 74 of the driver member 70 also has a square cross-sectional shape corresponding to the square cross-sectional shape of the main shaft portion 88 so that when the rotatable shaft 56 rotates, the main shaft portion 88 engages the threaded portion 74 of the driver member 70 to rotate the threaded portion 74. While the embodiment shown in FIG. 5 employs square cross-sectional shapes for the main shaft portion 88 and the driver lumen 82 through the threaded portion 74, in other embodiments, other non-circular shapes may be employed, including elliptical, rectangular, pentagonal, hexagonal, cross-recess, or star shapes.

Returning to FIG. 3, the rotatable shaft 56 can be a one-piece structure including a main shaft portion 88, a proximal shaft portion 90 on a proximal end of the main shaft portion 88, and a distal shaft portion 92 extending distally from the main shaft portion 88. The distal shaft portion 92 is narrower than a diameter of the recess 67 of the housing lumen 62. The shaft 56 can extend through most of the housing 52, from the proximal end 58 to the recess 57 adjacent to the distal end 60. In some embodiments, at least a portion of main shaft portion 88 and the proximal shaft portion 90 can extend proximally from the proximal end 58 of the housing 52. In some embodiments, the proximal shaft portion 90 can include a stylet engagement structure 96 so that the stylet 50 can engage the fixation device 38, as shown in FIG. 3. The stylet engagement structure 96 can be a slot, as shown, to engage a flat-bladed stylet, or can be other shapes to engage other types of styles, such as a cross-recess, a hexagonal recess, or a star recess.

In some embodiments, the shaft 56 can be made of a biocompatible metal, for example, stainless steel, Elgiloy, MP35N, or titanium. In other embodiments, the shaft 56 can be made of a biocompatible polymer that is rigid at body temperature, such as polyetheretherketone (PEEK) or polyethersulfone (PES). In still other embodiments, the shaft 56 can be made of a combination of the biocompatible metal and the biocompatible polymer. The shaft 56 can be formed by, for example, molding, machining, or 3D additive manufacturing.

The electrode assembly 48 can have an axis B that is collinear with the longitudinal axis A of the housing lumen 62. The electrode assembly 48 can include an anode electrode 96, a conical tip electrode 98, and an insulator 100. The anode electrode 96 is proximal of the conical tip electrode 98. The insulator 100 provides a spacing S between the anode electrode 96 and the conical tip electrode 98 to electrically isolate the anode electrode 96 from the conical tip electrode 98. In some embodiments, the spacing S can be as small as 1 mm, 1.5 mm, 2 mm, 2.5 mm, or 3 mm, or as large as 4 mm, 5 mm, 6 mm, 8, mm or 10 mm, or be any value between any two of the foregoing values, for example, between 1 mm and 10 mm, 1.5 mm and 8 mm, 2 mm and 6 mm, 2.5 mm and 5 mm, 3 mm and 4 mm, or 1 mm and 3 mm. The spacing S is measured from the anode electrode 96 to the conical tip electrode 98 along the axis B. It is believed that the electrode assemblies 48 having the spacing S in accordance with embodiments of the disclosure provide bipolar electrode functionality with a higher current density at the bundle of His 26 (FIG. 1) for more accurate sensing and pacing.

The anode electrode 96 and the conical tip electrode 98 can be made of a biocompatible metal, such as those described above in reference to the shaft 56, or a biocompatible conductive polymer, for example, a biocompatible polymer doped with a bio compatible conductive material, such as carbon, titanium, platinum, or gold. In some embodiments, the anode electrode 96 and the conical tip electrode 98 can be coated with an electrical surface multiplier, such as iridium oxide or titanium nickel, to improve sensing and pacing. In some embodiments, the anode electrode 96 and the conical tip electrode 98 can be coated with an antimicrobial coating, for example, polyethylene glycol. In some embodiments, the conical tip electrode 98 can be sharpened as shown in FIG. 3 to enable better penetration into the tissues of the heart 16 and contact the bundle of His 26 (FIG. 1).

In some embodiments, each of the anode electrode 96 and the conical tip electrode 98 can have a surface area as small as $0.5 \text{ mm}^2$, $1 \text{ mm}^2$, $1.5 \text{ mm}^2$, $2 \text{ mm}^2$, or as large as $2.5 \text{ mm}^2$, $3 \text{ mm}^2$, $4 \text{ mm}^2$, or $5 \text{ mm}^2$, or any value between any two of the foregoing values, for example $0.5 \text{ mm}^2$ to $5 \text{ mm}^2$, $1 \text{ mm}^2$ to $4 \text{ mm}^2$, $1.5 \text{ mm}^2$ to $3 \text{ mm}^2$, $2 \text{ mm}^2$ to $2.5 \text{ mm}^2$, or $2 \text{ mm}^2$ to $4 \text{ mm}^2$.

In some embodiments, the insulator 100 can be made of a biocompatible polymer that is rigid at body temperature, such as PEEK or PES. In some other embodiments, the insulator 100 can be made of a biocompatible ceramic. In some embodiments, the insulator 100 can be drug eluting, containing a drug to improve electrical performance by discouraging fibrous tissue formation around the electrode assembly 48. In some embodiments, the insulator 100 can include a radiopaque material to improve radiopacity of the electrode assembly 48.

As shown in FIG. 3, the first electrical conductor 44 and the second coil conductor 45 are filars of a bifilar coil conductor extending from the terminal pin 45 to the fixation device 38 at the distal end 42 (FIG. 2). At the fixation device 38, the individual filars of the first electrical conductor 44 and the second coil conductor 45 pass through the housing 52 to the electrode assembly 48, as shown more clearly in FIGS. 6 and 7, described below, to electrically connect electrode assembly 48 to the pulse generator 12 (FIG. 1). Specifically, the first electrical conductor 44 passes through first passage 102 to electrically connects the conical tip electrode 98 to the pulse generator 12 and the second electrical connector 45 passes through second passage 104 to electrically connect the anode electrode 96 to the pulse generator 12. In the embodiment shown in FIG. 3, the anode electrode 96 is a ring electrode and the first electrical connector 44 passes through the anode electrode 96 and the insulator 100 to connect to the conical tip electrode 98. The first electrical connector 44 and the second electrical connector 45 can be attached to the conical tip electrode 98 and the anode electrode 96 by, for example, crimping, bonding with a conductive eutectic alloy, bonding with a conductive adhesive, or welding (AC, DC, or ultrasonic). The electrode assembly 48 can be attached to the distal end 60 of the housing 52 by, for example, crimping, swaging, soldering, brazing, or welding (AC, DC, spin, laser, or ultrasonic).

Considering FIGS. 3-5 together, the fixation device 38 can be made by attaching the at least one tine 68 to the at least one lobe 84 of the carrier member 72, as described above. The hub 78 extending from the threaded portion 74 of the driver member 70 can be inserted through the carrier lumen 86. The flange 76 can be formed at an end of the hub 78 opposite the threaded portion 74, as described above, such that the carrier member 72 is rotatable about the hub 78, and the flange 76 and the threaded portion 74 restrain the axial movement of the carrier member 72. The at least one tine 68 can be inserted into the at least one slot 66 at the proximal end 58 of the housing 52 in the linear configuration. The at least one tine 68 is constrained by the housing 52 to prevent it from self-biasing back to the curved configuration. The carrier member 72 is inserted into the housing lumen 62 as the at least one lobe 84 slides within the at least one slot 66. The threaded portion 74 of the drive member 70 is threaded into the internal screw threads 64 at the proximal end 58 of the housing 52. The shaft 56 is inserted through the driver lumen 82 of the driver member 70 at the proximal end 58 of the housing 52 until the movement of the shaft 56 in the direction of the distal end 60 is limited by the recess 67 of the housing lumen 62 which prevents further movement of the main shaft portion 88. The first electrical connector 44 and the second electrical connector 45 are passed through the housing 52 and connected to the conical tip electrode 98 and the anode electrode 96, as described above. The electrode assembly 48 is connected to the distal end 60 of the housing 52, as described above.

In operation, the system 10 with the lead 14 having the fixation device 38 as described above, can be used in the undeployed state shown in FIG. 3 to map one of the locations described above in reference to FIG. 1 for accessing the bundle of His 26. The electrode assembly 48 can penetrate into the myocardium at a first spot near the bundle of His 26, measurements made, the electrode assembly 48 quickly removed from the myocardium and moved to a second spot where the process is repeated. The actions of penetrating the myocardium with the electrode assembly 48 by simply pushing on the lead 14 and removing the electrode assembly 48 from the myocardium by simply pulling on the lead 14 are faster and may cause less tissue damage than the prior art which required many turns of a helical electrode to either penetrate the myocardium or remove the electrode. Thus, embodiments of the disclosure can provide rapid and accurate mapping before positioning of the lead 14 close enough to the bundle of His 26 for efficient and effective pacing.

Once a suitable pacing location is found and the conical tip 100 of the electrode assembly 48 has penetrated the myocardium, the fixation device 38 can be deployed to fixate the lead 14. The fixation device 38 can be deployed by rotating stylet 50 in a first direction (e.g. clockwise) to rotate the shaft 56 as describe above. Rotating the shaft 56 in the first direction causes the tine assembly 54 to move through the housing 52 in the direction of the distal end 60. As the shaft 56 rotates, the driver member 70 also rotates as the main shaft portion 88 engages the driver lumen 82, as described above. The driver lumen 82 is sized to that the driver member 70 can slide along the shaft 56 while the main shaft portion 88 engages the driver lumen 82. The external threads 80 on the threaded portion 74 of the driver member 70 engage the internal screw threads 64 of the housing lumen 62, driving the driver member 70 toward the distal end 60. The driver member 70 pushes the carrier member 72 through the housing lumen 62, moving the attached at least one tine 68 through the at least one slot 66 to transition the at least one tine 68 from the linear configuration to the curved configuration. Because the carrier member 72 is rotatably disposed around the driver member 70, the carrier member 72 need not rotate with the driver member 70. However, frictional forces between the driver member 70 and the carrier member 72 may impart a slight rotational force on the carrier member 72. The at least one lobe 84 disposed in the at least one slot 66 prevents the carrier member 72 from rotating with the driver member 70 in response to the slight rotational force as the carrier member 72 moves through the housing lumen 62.

Figure 6:
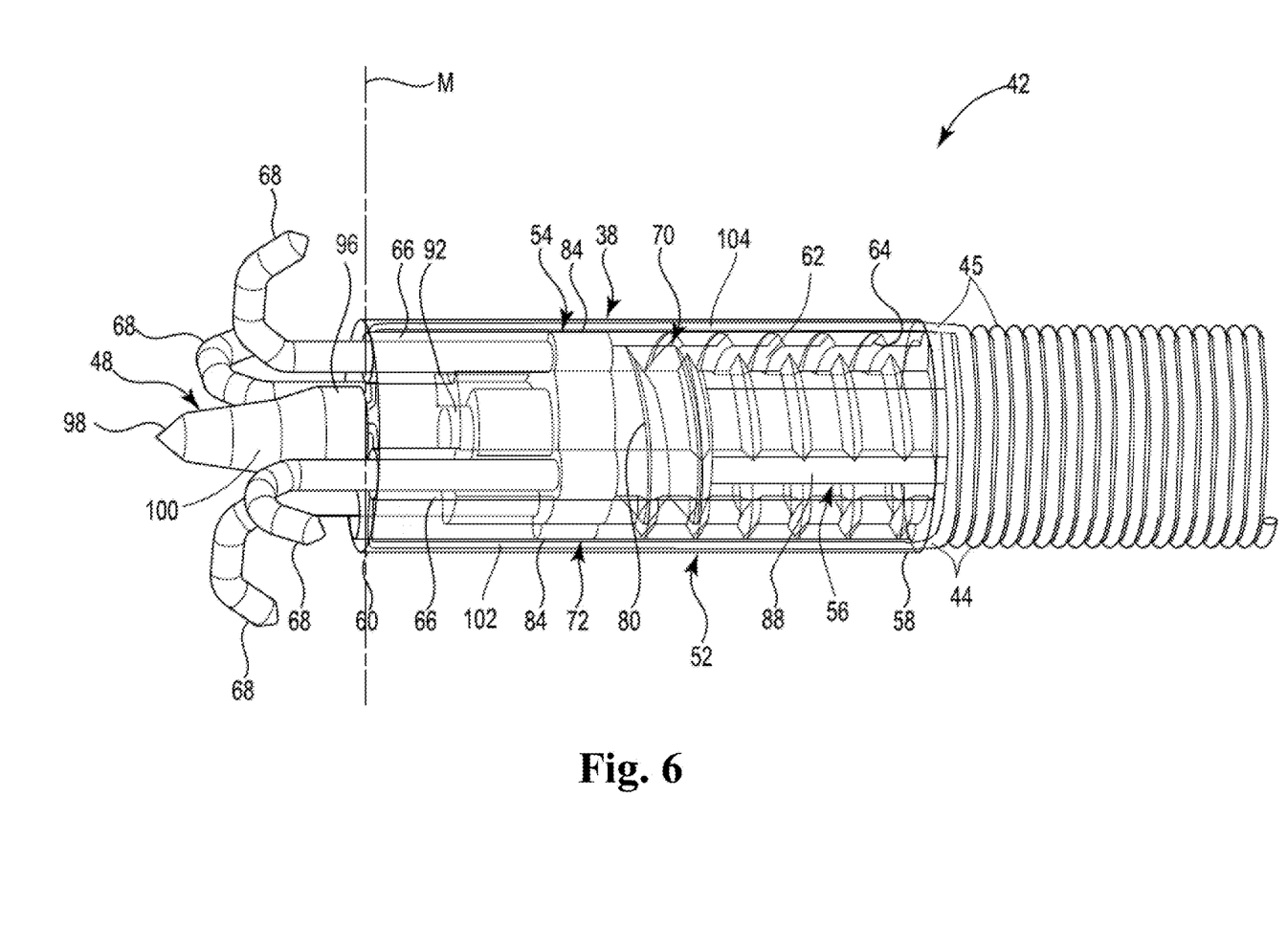
FIG. 6 is a perspective view of the device of FIG. 3 for the active fixation of the lead in a deployed state.

FIG. 6 is a perspective view of the fixation device 38 of FIG. 3 in a deployed state, according to embodiments of this disclosure. The lead body 34 is omitted for clarity. As each of the four tines 68 shown in FIG. 6 moves through one of the four slots 66 and begins to exit the housing 52 at the distal end 60, they transition from the liner configuration of FIG. 3 to the curved configuration shown in FIG. 6. Each of the tines 68 penetrates the myocardium M (position indicated with dotted line) and, unconstrained by the housing 52, self-biases to the curved configuration outside of the housing 52 as it penetrates through the myocardium M, carving a curved path through the myocardium M. In the embodiment shown in FIG. 6, each of the four tines 68 is oriented to self-bias to the curved configuration in a direction curving away from the electrode assembly 48. Other embodiments may have different orientations for the at least one tine 68. So deployed, the fixation device 38 fixates the lead 14 (FIG. 1) at the desired location.

Embodiments of the fixation device 38 may be less likely to move from the desired location than prior art devices. The electrode assembly 48 can begin to penetrate the myocardium M before the fixation device 38 is deployed, helping to stabilize the electrode assembly 48 during deployment. In addition, there should be little recoil from the force required to fixate the lead 14 because the tines 68 can deploy nearly straight out of the slots 66 and penetrate the myocardium M before substantially curving. As the tines 68 penetrate the myocardium M, they can pull the electrode assembly 48 further into the myocardium M such that the anode electrode 96 and the conical tip electrode 98 are both in secure contact with the myocardium M.

If desired, the fixation device 38 may be removed from the myocardium M by rotating the shaft 56 in a second direction opposite the first direction (e.g. counter-clockwise). Rotating the shaft 56 in the second direction causes the tine assembly 54 to move through the housing 52 in the direction of the proximal end 58. As the shaft 56 rotates, the driver member 70 rotates as the external threads 80 on the threaded portion 74 of the driver member 70 engage the internal screw threads 64 of the housing lumen 62, to drive the driver member 70 toward the proximal end 58. The driver member 70 pulls the carrier member 72 through the housing lumen 62, pulling the attached four tines 68 out of the myocardium M and back into their respective slots 66. Once the four tines 68 are out of the myocardium M, the electrode assembly 48 can be pulled from the myocardium M to remove the fixation device 38.

Figure 7:
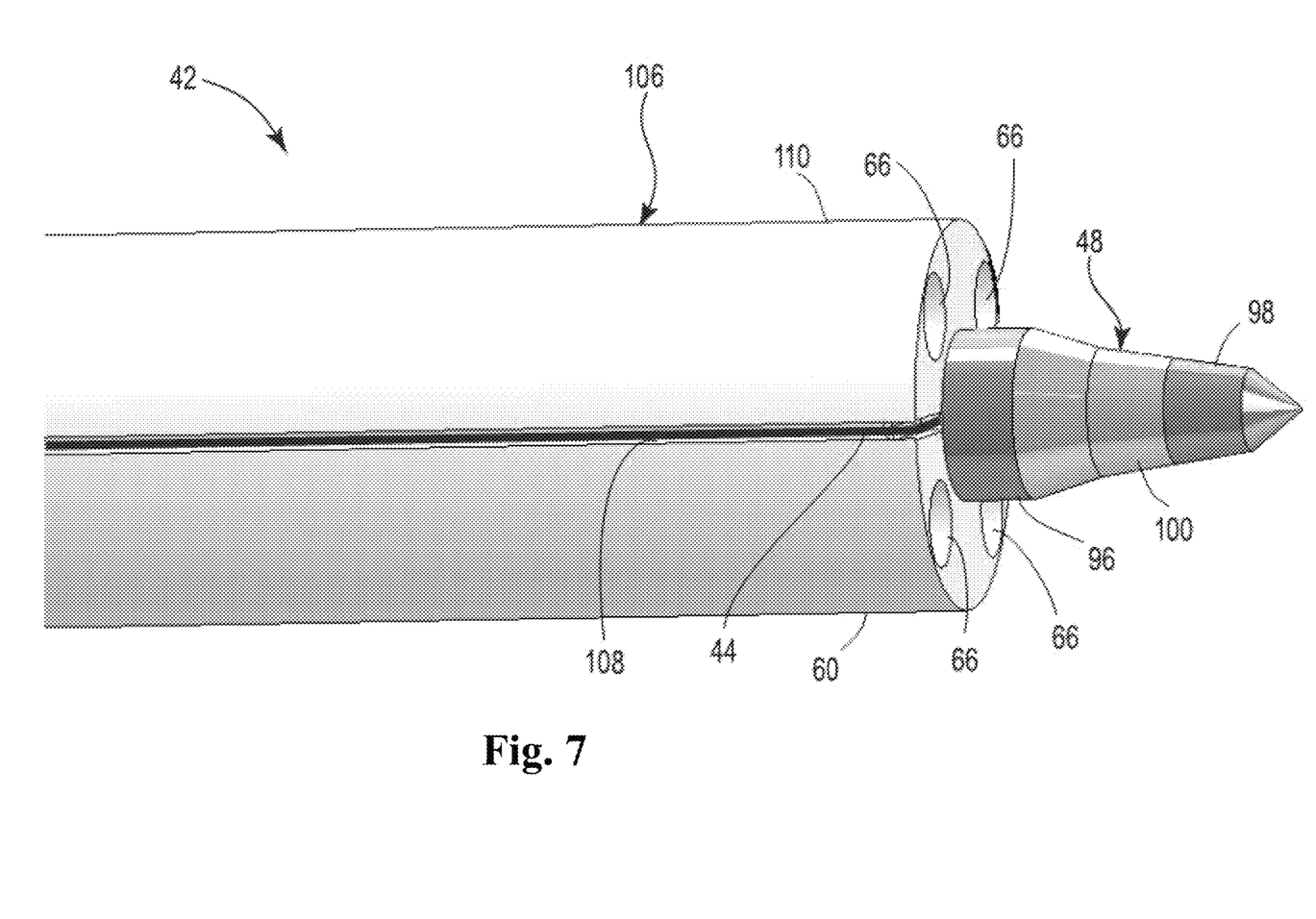
FIG. 7 is schematic perspective view of a distal end of the lead of FIG. 2 including another device for the active fixation of the lead, according to embodiments of this disclosure.

As shown in the embodiment of FIG. 6, the first electrical conductor 44 and the second electrical conductor 45 can pass through the first passage 102 and the second passage 104, respectively, within the housing 52 to electrically connect to the electrode assembly 48. FIG. 7 is schematic perspective view of a distal end 42 of the lead 14 of FIG. 2 including a fixation device 106 for the active fixation of the lead 14, according to embodiments of this disclosure. The fixation device 106 can be identical to the fixation device 38 described above, except that embodiments described above in reference to FIGS. 3-6 above, except that in the fixation device 106, the first electrical conductor 44 and the second electrical conductor 45 pass through a first channel 108 second channel 110 (only the first channel 108 is visible in FIG. 7). The first channel 108 and the second channel 110 can be formed in an exterior surface of the housing 52. The embodiment shown in FIG. 7 may be easier to manufacture than the embodiments shown in FIGS. 3 and 6 as passing the first conductor 44 and the second conductor 45 through the first channel 108 and the second channel 110 may be substantially easier than passing the first conductor 44 and the second conductor 45 through the first passage 102 and the second passage 104 within the housing 52. In some embodiments, the first conductor 44 and the second conductor 45 may be sealed into their respective first channel 108 or second channel 110 by, for example, an adhesive (epoxy, silicone, or polyurethane), an RF melted polymer, and/or a separate polymer piece RF welded or glued into place.

In the embodiments described above and shown in the FIGS. 1-7, the at least one tine 68 consists of four tines 68, the at least one slot 66 consisted of four slots 66 and the at least one lobe 84 consisted of four lobes 84. However, it is understood that embodiments can include only a single tine 68 or a plurality of tines 68, including 2, 3, 5, 6, 7, 8, 9, or 10 or more tines 68. It is further understood that embodiments can include only a single slot 66 or a plurality of slots 66, so long as the number of slots 66 is at least equal to the number of tines 68. It is further understood that embodiments can include only a single lobe 84 or a plurality of lobes 84.

In the embodiments described above and shown in FIGS. 1-7, the anode electrode 96 and the conical tip electrode 98 are shown as single electrodes. However, it is understood that the anode electrode 96 and the conical tip electrode 98 can each independently consist of a plurality of electrodes, each electrically isolated from each other and individually electrically connected to the pulse generator 12 by different electrical conductors. For example, in some embodiments, the anode electrode 96 can be a circumferential electrode array of two or more electrodes, instead of a single ring electrode, with each electrode of the circumferential electrode array independently electrically connected to the pulse generator 12. So configured, the pulse generator 12 can sense each electrode of the circumferential electrode array independently and select the anode electrode providing the best capture of the bundle of His 26. The anode electrode with the best capture can be used to pace the bundle of His 26, providing for a higher current density at the His bundle compared to a ring electrode. In this way, the current can be "steered" to provide a desired, or optimal, His bundle pacing capture response and/or restoration of cardiac conduction.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A device for the active fixation of an implantable medical lead into tissue, the device comprising:
    a housing including a proximal end for connecting to the lead and a distal end opposite the proximal end, the housing defining a housing lumen having a longitudinal axis, the housing lumen extending between the proximal end and a recess adjacent to the distal end;
    a tine assembly disposed within the housing lumen, the tine assembly including at least one tine configured to self-bias from a linear configuration within the housing to a curved configuration outside of the housing;
    an electrode assembly disposed at the distal end of the housing, the electrode assembly including:
        a conical tip electrode; and
        an anode electrode proximal of the conical tip electrode; and
    a rotatable shaft extending through the housing lumen, the shaft configured to engage the tine assembly such that rotation of the shaft transitions the at least one tine between the linear configuration and the curved configuration.

2. The device of claim 1, wherein rotation of the shaft in a first direction moves the at least one tine out of the housing lumen, transitioning the at least one tine from the linear configuration to the curved configuration to fix the lead to tissue, and rotation of the shaft in a second direction opposite the first direction retracts the at least one tine into the housing lumen, transitioning the at least one tine from the curved configuration to the linear configuration to release the lead from tissue.

3. The device of claim 1, wherein a proximal end of the shaft includes a structure for engaging a stylet.

4. The device of claim 1, wherein the at least one tine includes a plurality of tines.

5. The device of claim 1, wherein the anode electrode is electrically isolated from the conical tip electrode.

6. The device of claim 1, wherein the electrode assembly is collinear with the longitudinal axis of the housing lumen.

7. The device of claim 1, wherein the housing further includes internal screw threads extending along the housing lumen, and the tine assembly further includes:
    a driver member disposed within the housing lumen, the driver member defining a driver lumen coaxial with the housing lumen, the driver member including:
        a threaded portion having external screw threads engaged with the internal screw threads of the housing;
        a flange; and
        a hub connecting the flange to the threaded portion; and
    a carrier member rotatably disposed around the hub of the driver member, the at least one tine connected to and projecting from the carrier member, wherein the rotatable shaft extends through the driver lumen, the shaft configured to engage the driver member such that rotation of the shaft rotates the driver member to transition the at least one tine between the linear configuration and the curved configuration.

8. The device of claim 7, wherein the flange and the threaded portion of the driver member constrain axial movement of the carrier member.

9. The device of claim 7, wherein the housing further defines at least one slot at least partially radially outward from the internal screw threads, the at least one slot extending from the proximal end to the distal end and parallel to the longitudinal axis.

10. The device of claim 9, wherein the carrier member includes at least one lobe configured to engage the at least one slot to prevent axial rotation of the carrier member relative to the housing while permitting the carrier member to move through the housing lumen while the shaft rotates the driver member, the at least one tine connected to and projecting from the at least one lobe.

11. The device of claim 7, wherein the driver lumen is sized so that the driver member can slide along the shaft while the shaft rotates the driver member.

12. An implantable medical lead comprising:
a flexible, tubular lead body including a proximal end and a distal end;
a connector assembly connector disposed at the proximal end;
a plurality of electrical conductors extending through the tubular body from the connector assembly to the distal end; and
a device for the active fixation of the implantable medical lead, the device disposed at the distal end of the lead, the device including:
a housing including a proximal end for connecting to the lead and a distal end opposite the proximal end, the housing defining a housing lumen having a longitudinal axis, the housing lumen extending between the proximal end and a recess adjacent to the distal end;
a tine assembly disposed within the housing lumen, the tine assembly including at least one tine configured to self-bias from a linear configuration within the housing to a curved configuration outside of the housing;
an electrode assembly disposed at the distal end of the housing, the electrode assembly including:
a conical tip electrode electrically connected to at least one of the plurality of electrical conductors; and
an anode electrode proximal of the conical tip electrode, the anode electrode electrically connected to at least one of the plurality of electrical conductors different from the at least one of the plurality of electrical conductors electrically connected to the conical tip electrode; and
a rotatable shaft extending through the housing lumen from the proximal end to the recess adjacent to the distal end, the shaft configured to engage the tine assembly such that rotation of the shaft transitions the at least one tine between the linear configuration and the curved configuration.

13. The lead of claim 12, wherein the at least one tine includes a plurality of tines.

14. The lead of claim 12, wherein the anode electrode is electrically isolated from the conical tip electrode.

15. The lead of claim 12, wherein the housing further includes internal screw threads extending along the housing lumen, and the tine assembly further includes:
a driver member disposed within the housing lumen, the driver member defining a driver lumen coaxial with the housing lumen, the driver member including:
a threaded portion having external screw threads engaged with the internal screw threads of the housing;
a flange; and
a hub connecting the flange to the threaded portion; and
a carrier member rotatably disposed around the hub of the driver member, the at least one tine connected to and projecting from the carrier member, wherein the rotatable shaft extends through the driver lumen, the shaft configured to engage the driver member such that rotation of the shaft rotates the driver member to transition the at least one tine between the linear configuration and the curved configuration, and the flange and the threaded portion of the driver member constrain axial movement of the carrier member.

16. The lead of claim 15, wherein the housing further defines at least one slot at least partially radially outward from the internal screw threads, the at least one slot extending from the proximal end to the distal end and parallel to the longitudinal axis, and the carrier member includes at least one lobe configured to engage the at least one slot to prevent axial rotation of the carrier member relative to the housing while permitting the carrier member to move through the housing lumen while the shaft rotates the driver member, the at least one tine connected to and projecting from the at least one lobe.

17. A method of making a device for the active fixation of an implantable medical lead, the method comprising:
attaching at least one tine to a carrier member, the tine self-biasing to a curved configuration;
inserting a hub extending from a threaded portion of a driver member through the carrier member such that the carrier member is rotatable about the hub;
forming a flange at an end of the hub opposite the threaded portion of the driver member, the flange and the threaded portion of the driver member restraining the axial movement of the carrier member;
inserting the at least one tine into a proximal end of a longitudinal slot of a housing lumen of a housing to place the at least one tine in a linear configuration contained by the housing;
threading the threaded portion of the drive member into a threaded portion at a proximal end of the housing;
inserting a shaft through the a driver lumen of the driver member at the proximal end of the housing and through the housing lumen to a recess adjacent to a distal end of the housing; and
connecting an electrode assembly to the distal end of the housing, the electrode assembly including a plurality of electrodes.

18. The method of claim 17, further including electrically connecting each of the plurality of electrodes to separate electrical conductors.

19. The method of claim 17, wherein forming the flange at the end of the hub includes:
heating the end of the hub until it softens; and
flanging the heated hub outward to form the flange.

20. The method of claim 17, wherein forming the flange at the end of the hub includes connecting the flange to the end of the hub.

* * * * *